United States Patent [19]

Hashimoto

[11] Patent Number: 4,975,940

[45] Date of Patent: Dec. 4, 1990

[54] TELEPHONE RINGING ADAPTER FOR OPERATING UPON RECEPTION OF A PRESET NUMBER OF CALLING SIGNALS

[75] Inventor: Kazuo Hashimoto, Tokyo, Japan

[73] Assignee: Hashimoto Corporation, Tokyo, Japan

[21] Appl. No.: 822,296

[22] Filed: Jan. 24, 1986

[30] Foreign Application Priority Data

Jan. 25, 1985 [JP] Japan .................................. 60-12090

[51] Int. Cl.⁵ .............................................. H04M 1/65
[52] U.S. Cl. ........................................ 379/67; 379/82; 379/373; 379/442
[58] Field of Search .................... 379/82, 67, 373, 442

[56] References Cited

U.S. PATENT DOCUMENTS

| 4,049,916 | 9/1977 | Danner | 379/82 X |
| 4,066,848 | 1/1978 | Darwood | 379/82 X |
| 4,496,797 | 1/1985 | Price | 379/82 X |
| 4,577,063 | 3/1986 | Hanscom et al. | 379/82 |

FOREIGN PATENT DOCUMENTS 49-5162  2/1974  Japan .

OTHER PUBLICATIONS

"Unanswered Call Diverter", R. L. Brady et al., *IBM Tech. Discl. Bulletin*, vol. 25, No. 7A, Dec. 1982, pp. 3480, 3481.

Primary Examiner—Thomas W. Brown
Attorney, Agent, or Firm—Lowe, Price, LeBlanc, Becker & Shur

[57] ABSTRACT

A telephone ringing adapter has a preset number of ringing tones of a calling signal applied from a telephone call diverting device or the like. When the incoming ringing number coincides with the preset number, a relay is energized so that the calling signal is applied to a conventional telephone answering device which is connected to the adapter to comprise a loop circuit and take a message from the calling party. After the hang-up of the calling party, the relay is released and it returns to standby mode for the next call. So, even when the final call diverted party doesn't answer the call, it is possible for a general telephone answering device to operate the automatic answering and recording function for the calling party after the preset number of calling signals.

5 Claims, 2 Drawing Sheets

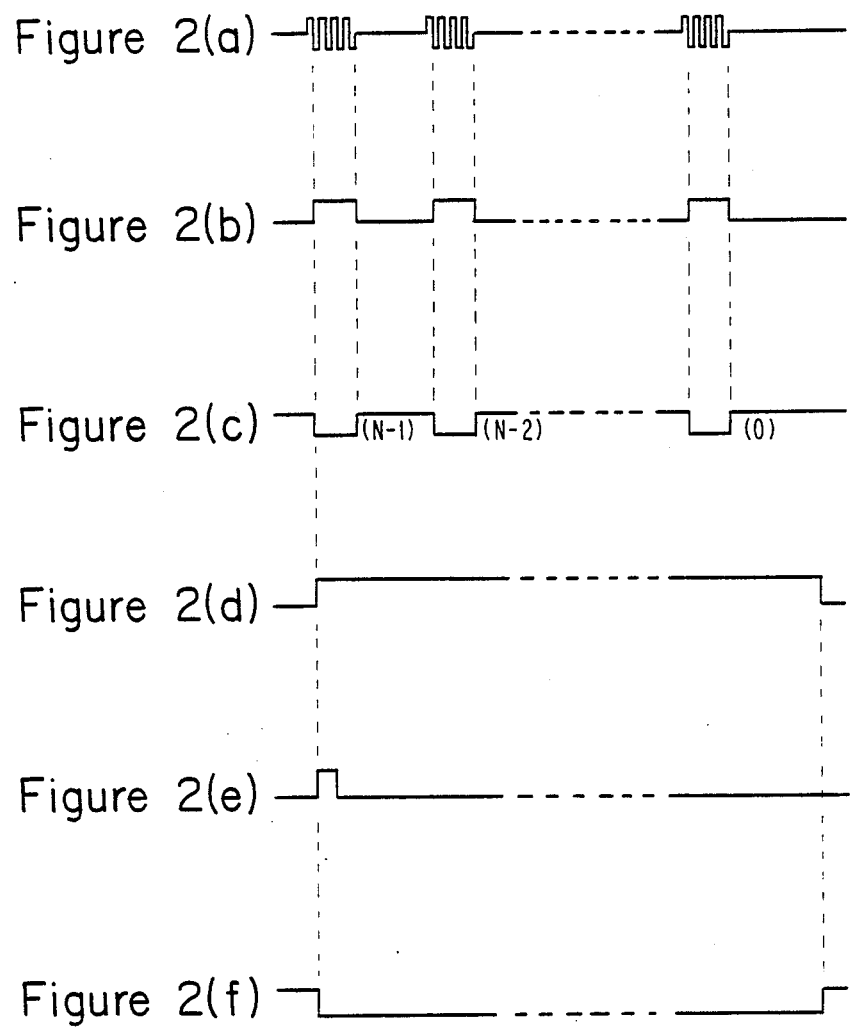

TELEPHONE RINGING ADAPTER FOR OPERATING UPON RECEPTION OF A PRESET NUMBER OF CALLING SIGNALS

BACKGROUND OF THE INVENTION

Some conventional telephone answering devices are capable of setting the ringing counter circuit which counts calling signals and operates upon receiving the preset number of ringing or calling signals. These devices, however, are incapable of energizing after counting the precise number of rings, for example, twenty-three rings or forty-four rings. For instance, in the case of connecting a call diverting device with a telephone answering device, in order to operate the telephone answering device automatically when a call diverted party cannot answer the call, there must be means which operates the telephone answering device if the call diverted party doesn't answer the call after dozens of ringing signals. The conventional means for setting the preset ringing counter which the telephone answering device itself contains is not actually capable of doing such an operation.

SUMMARY OF THE INVENTION

The present invention relates to a telephone ringing adapter which is adapted to a general telephone answering device and energizes it upon receiving the precise number of calling signals. It is an object of the present invention to provide a telephone ringing adapter which operates telephone equipment such as a telephone answering device upon receiving exactly the preset number, from 1 to 99 of the calling signals through the telephone line.

It is a second object of the invention to attain the above described function by connecting a simple adapter to a telephone answering device in tandem through a relay contact.

The above and other objects, features and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 2 is a timing chart starting when the calling signal arrives.

DESCRIPTION OF THE PREFERRED EMBODIMENT

Figure 1:
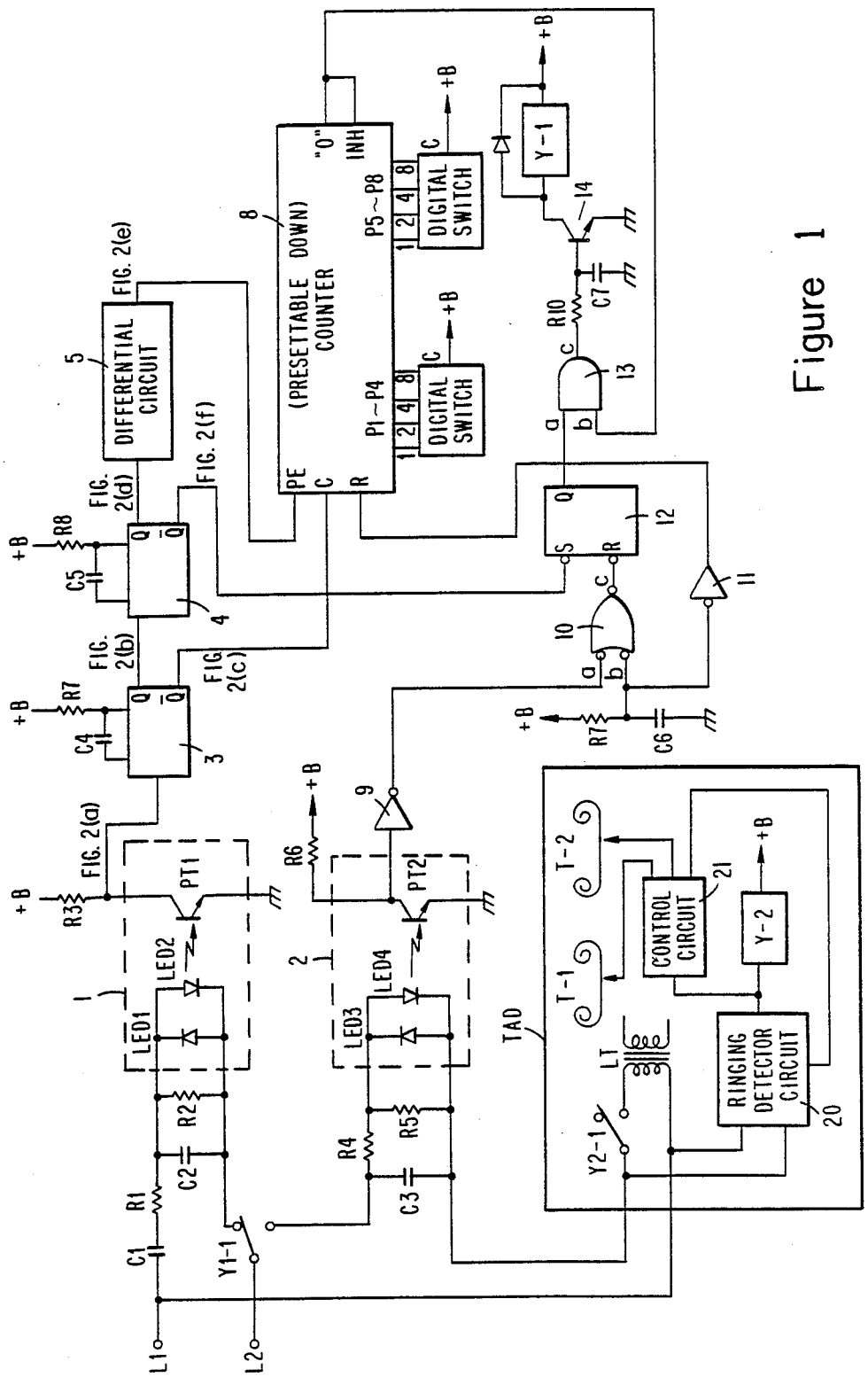
FIG. 1 is a circuit diagram of the present invention.

The arrangement and operations of the preferred embodiment according to the present invention will be described.

In FIG. 1, reference symbols L 1 and L 2 denote telephone lines. Reference numeral 1 denotes a photocoupler for detecting a calling signal. When a telephone answering device TAD mentioned later makes a loop circuit upon reception of a calling signal a photocoupler 2 is inserted into the said loop circuit in series and operates to make the present device return to the standby mode after the operations of the telephone answering device are finished and the calling party hangs up.

Reference numeral 3 denotes a re-trigger type monostable multivibrator (hereinafter called mono multi) which generates an output of H level while the calling signal (16 Hz) is being accepted. A mono multi 4 generates an output of H level upon an input of H level from the said mono multi 3 and keeps the said output of H level while the calling signal is being applied. When the output of the said mono multi 4 turns to H level from L level, a differential circuit 5 generates one pulse which is used as a pulse for presetting a counter 8 mentioned later.

Digital switches 6 and 7 are of the rotary type (which have from 0 to 9 numerals) and are connected to preset terminals of the counter 8, mentioned later. By using the digital switches, it is possible to preset the count number of the calling signal up to 99 at maximum. Reference numeral 8 denotes a presettable down counter (hereinafter called a counter) capable of counting down a maximum of 99 times. Two C-MOS MC 14522 elements are used in the present embodiment and there is provided a reset terminal R, preset terminals P1 to P4 and P5 to P8, a clock terminal C, a preset enable terminal PE, an output terminal "0" which generates an output of H level with the count 0 and an inhibit terminal INH which inhibits input to the said clock terminal at H level.

Reference numeral 9 denotes an inverter; 10, an OR gate; and 11, an inverter. An R-S type flip-flop circuit 12 is set by the output of the mono multi 4 and reset by the output of the photocoupler 2 when the calling party hangs up. Reference numeral 13 denotes an AND gate; and 14, a transistor. Reference symbol Y-1 denotes a relay having a transfer contact y1-1; and TAD, a telephone answering device which is on the market (only the main part concerned in the present invention is shown), wherein there is provided a ringing detector circuit 20 for detecting the calling signal, a relay Y-2 which is energized by the output of the said ringing circuit and has a contact y1-1, a control circuit 21, a line transformer LT, an outgoing message tape T-1 and an incoming message tape T-2.

Operation will be described. It is assumed that the TAD is arranged to operate when the calling signal (ring) stops ringing after, for instance, 20 rings. In this case, if the TAD itself operates when the calling signal stops ringing after 3 rings, the digital switches 6 and 7 are set at "17" (to be described in detail later). Further, when the present device is supplied electric power, the flip-flop circuit 12 is reset by effect of a capacitor C 6. The transistor 14 is not made conductive by the AND gate 13 and the relay Y-1 is not energized. In this state, when the calling signal appears at the telephone lines L 1 and L 2, through the capacitor C 1, resistor R 1, the light-emitting diode LED 1 or LED 2 (according to the polarity of 16 Hz) in the photocoupler 1 and the contact Y1-1, the said two light-emitting diodes are turned on alternately according to the calling signal. A photo transistor PT 1 receives its light of LED and re-trigger type mono multi 3 is triggered.

The wave form of the calling signal is shown as (a) in FIG. 2 and those of outputs (Q, $\bar{Q}$) of the said mono multi 3 as (b) and (c). At the same time, by output of the said mono multi 3 the re-trigger type mono multi 4 is triggered and the wave forms shown as (d) and (f) in FIG. 2 are outputted by outputs Q and $\bar{Q}$ of the mono multi 4. When the output Q of the mono multi 4 becomes H level from L level, one pulse shown as (e) in FIG. 2 is generated by the differential circuit 5. This pulse enters into the preset enable terminal PE of the counter 8 and the preset code ("17" as mentioned above) by the digital switches 6 and 7 is inputted into the said counter 8. Meanwhile, when the output $\bar{Q}$ of the mono multi 4 becomes L level as mentioned above, the flip-flop circuit 12 is set. By its output Q a terminal a of the AND gate 13 goes up to H level. A terminal b of the AND gate 13 is kept at the L level through a terminal "0" by the preset of the said counter 8. The terminal "0" becomes H level with the count 0 as mentioned later. Since the transistor 14 is not energized and the relay Y-1 is not energized, even after the above-mentioned preset of the counter 8, the calling signal continues to enter into the photocoupler 1 through the contact y1-1 placed as shown in the figure. Accordingly, when the first calling signal stops ringing, the preset count of the counter 8 becomes minus one (N-1 shown in (c) of FIG. 2) through the count terminal C upon changing the output $\bar{Q}$ of the mono multi 3 to H level from L level.

This operation is repeated upon stopping each ring of the calling signal. In the present embodiment, when the calling signal stops ringing after 17 rings, the said preset count becomes 0. The said terminal "0" is then changed to H level from L level and the relay Y-1 is energized through the AND gate 13, the resistor R 10 and the transistor 14.

Now the contact y1-1 of the relay Y-1 is switched on and the calling signal afterward is applied to the ringing detector circuit 20 of the telephone answering device TAD through the capacitor C 3. Further, the time constant of the capacitor C 3 is preset in order to prevent the calling signal from initially being applied to the photocoupler 2. Accordingly, when the said calling signal is applied, for instance, three times, the relay Y-2 is energized and the loop circuit is formed through the contact y 2-1 of Y-2 and the line transformer LT.

According to the polarity of the telephone line the light-emitting diode LED 3 or LED 4 is inserted into the loop circuit in series, so that the ringing is tripped and, the telephone answering device is engaged. Operation afterward is well-known, so the outgoing message is sent out from the outgoing message tape T-1 and after the outgoing message the incoming message tape T-2 starts driving to record the incoming message from the calling party. During the said recording, when the TAD returns to the standby mode, for example, by the function of a fixed timer (e.g. 30 seconds) before the calling party hangs up, the relay Y-2 gets non-energized through the control circuit 21 and the contact y2-1 opens.

As the light-emitting diode LED 3 OR LED 4 which was inserted into the loop circuit in series and turned on is then turned off, the photo transistor PT 2 which was energized becomes non-energized and the said flip-flop circuit 12 is reset through the inverter 9 and the OR gate 10. The relay Y-1 then becomes non-energized as described above clearly and the present device returns to the standby mode, awaiting the reception of the next call.

Meanwhile, when the telephone is on-hooked by the calling party himself during the above operation by the TAD, the loop current reduces by on-hooking of the calling party and the light-emitting diode LED 3 and LED 4 which was turned on is turned off, so that the relay Y-1 becomes deenergized as mentioned above. As the relay Y-1 is not energized, the loop circuit of the TAD is opened by y1-1 and then the telephone answering device returns to the standby mode by the momentary detecting circuit, the VOX circuit or the timer circuit which the TAD itself contains.

Although a certain preferred embodiment has been shown and described, it should be understood that many changes and modifications may be made therein without departing from the scope of the invention.

What is claimed is:

1. A telephone ringing adapter which operates upon receipt at a called party station of a preset number of incoming calling ring signals comprising:
   (a) first circuit means for accepting calling signals through a telephone line,
   (b) a digital counter which generates an output when said incoming calling ring signals coincide in number with said preset number,
   (c) relay means which is energized by said output from said digital counter,
   (d) a transfer relay contact of said relay means which changes connection of said calling signals from said circuit means to a telephone answering device at the called party station,
   (e) a ringing detector circuit of said telephone answering device which is energized by said calling signals after energization of said relay means,
   (f) outgoing message transmitting means operative after engagement of said telephone answering device,
   (g) incoming message recording means operative after said outgoing message transmitting means,
   (h) hang-up detecting circuit means which detects the hang-up of a calling party or an on-hook condition of the telephone answering device, for releasing said relay means to change over connection from said telephone answering device to said first circuit means, and
   (i) disengaging means of said telephone answering device for causing said detecting circuit means to effect release of said relay contact to establish a standby mode.

2. The telephone ringing adapter of claim 1, wherein said first circuit means comprises photocoupler means for detecting a calling signal.

3. The telephone ringing adapter of claim 2, wherein said first circuit means further comprises multivibrator means coupled to said photocoupler means for generating signal pulses in response to said calling signals.

4. The telephone ringing adapter of claim 3, wherein said multivibrator means is coupled to said digital counter for application of said signal pulses thereto.

5. The telephone ringing adapter of claim 1, wherein said hang-up detecting circuit means comprises photocoupler means.

* * * * *